US009179833B2

(12) United States Patent
Narasimha-Iyer et al.

(10) Patent No.: US 9,179,833 B2
(45) Date of Patent: Nov. 10, 2015

(54) SYSTEMS AND METHODS FOR IMPROVED EASE AND ACCURACY OF GAZE TRACKING

(71) Applicant: Carl Zeiss Meditec, Inc., Dublin, CA (US)

(72) Inventors: Harihar Narasimha-Iyer, Livermore, CA (US); Vincent Michael Patella, Albany, CA (US); Goeran Anders Johansson, San Francisco, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 87 days.

(21) Appl. No.: 13/781,051

(22) Filed: Feb. 28, 2013

(65) Prior Publication Data

US 2014/0240675 A1    Aug. 28, 2014

(51) Int. Cl.
*A61B 3/14* (2006.01)
*A61B 3/00* (2006.01)
(Continued)

(52) U.S. Cl.
CPC ............ *A61B 3/0025* (2013.01); *A61B 3/0091* (2013.01); *A61B 3/024* (2013.01); *A61B 3/113* (2013.01); *G06F 3/013* (2013.01);
(Continued)

(58) Field of Classification Search
CPC .............. A61B 3/0008; A61B 3/0091; A61B 3/10–3/1025; A61B 3/11; A61B 3/112; A61B 3/113; A61B 3/14–3/158; G06F 3/013
USPC .................................................. 351/206–211
See application file for complete search history.

(56) References Cited

U.S. PATENT DOCUMENTS

| 3,718,386 A | 2/1973 | Lynn et al. |
| 3,883,235 A | 5/1975 | Lynn et al. |

(Continued)

FOREIGN PATENT DOCUMENTS

| WO | 2008/139137 A1 | 11/2008 | |
| WO | WO 2008139137 A1 * | 11/2008 | ............. A61B 3/024 |
| WO | WO 2011117776 A1 * | 9/2011 | |

OTHER PUBLICATIONS

Hennessey et al., "A single camera eye-gaze tracking system with free head motion," In Proceedings of the 2006 symposium on eye tracking research & applications (ETRA 2006), ACM, New York, NY, USA, 87-94.*

(Continued)

*Primary Examiner* — Thomas K Pham
*Assistant Examiner* — Nicholas R Pasko
(74) *Attorney, Agent, or Firm* — Morrison & Foerster LLP (57) ABSTRACT

Methods for improving gaze tracking are presented. These methods eliminate the need for a separate initial calibration step to determine whether the subject is properly centrally fixated during testing. In one embodiment, whether the subject is centrally fixated is determined by identifying inlier and outlier gaze descriptors; the inliers are assumed to be associated with central fixation. This reduces the total time required for testing. These methods also improve the accuracy of gaze tracking during testing without the need for individual subject calibration. Instead, a database of reference eyes is used. The subject's eye can be compared to the reference eyes, and the mapping function for one or more reference matches can be used to estimate the subject's gaze direction. In another embodiment, previous calibration data from the same subject can be used to determine whether the subject is properly centrally fixated and/or the direction of the subject's gaze.

27 Claims, 5 Drawing Sheets

(51) Int. Cl.
*A61B 3/113* (2006.01)
*A61B 3/024* (2006.01)
*G06F 3/01* (2006.01)
*G06K 9/00* (2006.01)

(52) U.S. Cl.
CPC ............ *G06K9/00604* (2013.01); *A61B 3/0008* (2013.01); *A61B 3/0083* (2013.01)

(56) References Cited

U.S. PATENT DOCUMENTS

| | | | |
|---|---|---|---|
| 5,035,500 A | 7/1991 | Rorabaugh et al. | |
| 5,220,361 A | 6/1993 | Lehmer et al. | |
| 5,491,757 A | 2/1996 | Lehmer et al. | |
| 6,367,932 B1 | 4/2002 | Donaldson | |
| 6,393,136 B1 * | 5/2002 | Amir et al. | 382/103 |
| 6,578,962 B1 * | 6/2003 | Amir et al. | 351/209 |
| 6,659,611 B2 * | 12/2003 | Amir et al. | 351/210 |
| 7,306,337 B2 * | 12/2007 | Ji et al. | 351/209 |
| 7,533,989 B2 * | 5/2009 | Ebisawa | 351/208 |
| 7,600,873 B2 * | 10/2009 | Grundig | 351/210 |
| 7,717,561 B2 * | 5/2010 | Knaan et al. | 351/210 |
| 7,805,009 B2 * | 9/2010 | Everett et al. | 382/218 |
| 7,809,160 B2 * | 10/2010 | Vertegaal et al. | 382/103 |
| 8,032,842 B2 * | 10/2011 | Kwon et al. | 715/850 |
| 8,132,916 B2 | 3/2012 | Johansson | |
| 2007/0265507 A1 | 11/2007 | de Lemos | |
| 2010/0149488 A1 * | 6/2010 | Lo et al. | 351/206 |
| 2011/0182472 A1 * | 7/2011 | Hansen | 382/103 |
| 2011/0228975 A1 * | 9/2011 | Hennessey et al. | 382/103 |
| 2012/0147328 A1 * | 6/2012 | Yahav | 351/210 |
| 2012/0162603 A1 * | 6/2012 | Dejima | 351/209 |
| 2012/0274905 A1 | 11/2012 | Johansson et al. | |
| 2013/0002846 A1 * | 1/2013 | De Bruijn et al. | 348/78 |
| 2013/0114850 A1 * | 5/2013 | Publicover et al. | 382/103 |
| 2013/0145304 A1 * | 6/2013 | DeLuca et al. | 715/781 |
| 2013/0188834 A1 * | 7/2013 | Ebisawa | 382/103 |
| 2014/0320397 A1 * | 10/2014 | Hennessey et al. | 345/156 |

OTHER PUBLICATIONS

Hennessey et al., "Improving the Accuracy and Reliability of Remote System-Calibration-Free Eye-gaze Tracking", IEEE Transactions on Biomedical Engineering, vol. 56, No. 7, Jul. 2009, pp. 1-10.

Lu et al., "Gaze Tracking by Binocular Vision and LBP Features", International Conference on Pattern Recognition, IEEE, 2008, 4 pages.

International Search Report and Written Opinion received for PCT Patent Application No. PCT/EP2014/053885, mailed on May 20, 2014, 12 pages.

* cited by examiner

SYSTEMS AND METHODS FOR IMPROVED EASE AND ACCURACY OF GAZE TRACKING

TECHNICAL FIELD OF THE INVENTION

This invention relates to the field of gaze tracking. In particular, the invention discloses methods for improving the ease and accuracy of gaze tracking methods. These methods are particularly useful for visual field testing or perimetry.

BACKGROUND

Perimetry measures the central and peripheral visual fields to detect vision loss. While the subject fixates on a central target, test stimuli are presented at different locations in the field of view. The subject indicates if he or she sees the test stimulus. In static perimetry, a first stimulus is presented at a chosen location; if the subject does not see the stimulus, the size or intensity of the test object is increased in later presentations at the same location until the subject sees it. If the initial stimulus is seen, then stimulus size or intensity is decreased in subsequent presentations at the same location until not seen. This is repeated at a series of locations to determine the sensitivity of the visual field at each. In kinetic perimetry, the same test stimulus is moved from a peripheral area toward the center until the subject sees it. This is done from multiple directions, determining a boundary within which the subject can see the stimulus and outside of which the subject cannot see it. This can be repeated with multiple test stimuli.

Maintaining steady fixation on the central target is vital to accurate mapping of the visual field and for comparing follow-up tests over time. However, the full test procedure is often lengthy, and subjects may experience fatigue during the testing, making it difficult to maintain central fixation. Moreover, as the test stimulus is moved, a subject's natural inclination may be to move his or her gaze toward the stimulus rather than maintaining central fixation. Information regarding the subject's fixation during the test may be incorporated into the test results. The commercially available HFA II-i (Carl Zeiss Meditec, Inc. Dublin, Calif.) provides a graphical display of the gaze tracking output over time. The display indicates a magnitude of deviation but provides no information on where the subject is actually looking. In another method, the clinician may be given images of the patient's eye during each stimulus presentation, so the clinician can determine not only gaze but also whether there were other detractors, such as blinking (see U.S. Publication No. 2012/0274905 to Johansson, et al.).

Current protocols for perimetry typically require certain initial steps for calibrating gaze information. First, they may require an initial step that allows the system to determine whether the subject is properly centrally fixated during the presentation of test stimuli. During this step, the subject is generally instructed to fixate at a central location. In one type of gaze tracker used in the HFA II-i, a light source is used to create a reflection from the subject's cornea while the subject fixates at the central location. The spatial relationship between this corneal reflection and the location of the eye's pupil is then later used to determine whether, during the presentation of test stimuli, the subject appropriately maintains central fixation. Other gaze tracking designs may rely upon location of different ocular landmarks, but all require some sort of initial zero-point calibration in order to correct for normal anatomical variability from patient to patient. This initial calibration step takes anywhere from just a few seconds to tens of seconds and increases the total time required to complete a visual field examination. Thus, a method of gaze tracker calibration that can be accomplished in the normal course of test stimuli presentation during visual field testing, instead of before visual field testing, is desirable.

Some protocols may also include another calibration step that allows the system to more accurately determine the direction of the subject's gaze during the presentation of each stimulus, not just whether the gaze deviates from the central fixation point. In protocols seeking to have highly accurate gaze tracking, the subject may need to perform a lengthy calibration process in which an ocular reflection is tracked on the eye while the subject looks individually at each of a number of different reference locations. This determines a mapping function between a vector defined by the reflection and pupil location, versus the subject's gaze direction.

Because this calibration step is time-consuming for the subject to perform, many protocols do not acquire calibration data for each individual subject. Instead, they use a single mapping function to predict all subjects' gaze behavior. Relying on the same mapping function for all subjects, however, can be a source of error. The shape of subjects' eyes may vary from the reference eye, making the gaze estimates based on the reference eye's mapping function inaccurate.

Some gaze-tracking methods have been proposed to avoid this source of error while also avoiding time-consuming individual calibration steps. However, these methods require the use of multiple cameras and accurate camera calibration during manufacturing, adding significant cost to the system. Thus, a method that does not introduce errors through use of a single reference eye, while not adding to subject testing time, but also that does not require costly modifications to a diagnostic system, is highly desirable.

SUMMARY

Eliminating the Initial Calibration Step

This invention provides a method for determining whether the subject is properly centrally fixated during test stimuli presentation without a separate initial calibration step. By removing the initial step, the invention reduces the total time required for the visual field examination. Instead of requiring the subject to sit through this initial step, this invention uses all or a subset of the gaze information collected during the presentation of the test stimuli to determine the characteristics of the subject's gaze associated with central fixation. This is done by analyzing all or a subset of the gaze information to determine inliers and outliers. Because the subject has been instructed to fixate centrally, the inliers can be assumed to be associated with test stimuli during which the subject was centrally fixated, while the outliers can be assumed to be associated with test stimuli during which the subject's gaze deviated from the center point. In some embodiments, this invention may use previously acquired calibration data from the same subject to provide a provisional calibration. The provisional calibration may be then verified or refined, or used as additional information in determining the characteristics of the subject's gaze associated with central fixation.

Increasing the Accuracy of Gaze Estimation

The current invention also provides a method for improving the accuracy of gaze estimation during testing. As described above, current methods for gaze tracking generally rely on predetermined calibration data from a single model or reference eye and typically only report on deviation from central fixation, not where the subject is actually looking.

While using predetermined calibration data from a reference eye reduces the time required for individual testing, it can introduce error because the calibration data is not applicable to all eyes. The current invention avoids the error associated with using a single reference eye and thus improves accuracy, but also avoids the need for lengthy gaze calibrations for each of the subject's eyes as part of the visual field testing protocol. The improved accuracy gaze estimation can be used to filter out bad data or reassign data to the correct location prior to analysis to improve the accuracy in the visual field test results.

In one embodiment, this is done by building a database of reference eyes having different corneal topologies. When a subject undergoes visual field testing, the subject's corneal shape is then compared to the shape of the reference eyes in the database to find one or more matches. The calibration data from the match or matches is then used to estimate the gaze of the subject's eye. This technique can be done using a simple system setup with a single camera and multiple illuminators to create ocular reflections (also called reflexes). Using an image taken while a subject's eye is centrally fixated, the pupil center and ocular reflexes are segmented. Vectors from the pupil center to the ocular reflexes are determined, which serve as the shape descriptor. This shape descriptor can then be compared against the shape descriptors in the reference database. The eye (or eyes) in the reference database that is closest in shape to the subject's eye is selected, and that reference eye's calibration data can then be used to estimate the gaze of the subject's eye during presentation of test stimuli. Additionally or alternatively, in some embodiments, previously acquired calibration data can be used for gaze estimation.

DETAILED DESCRIPTION

Figure 1:
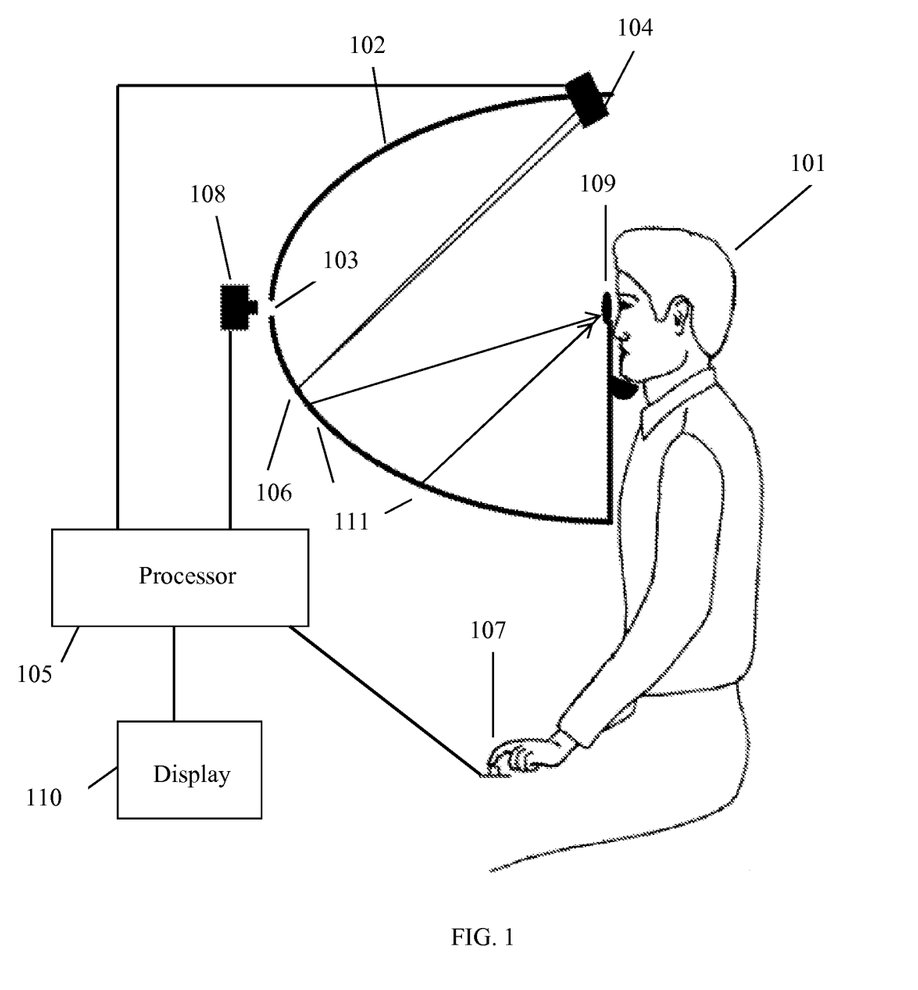
FIG. 1 illustrates one example of a visual field test instrument that can be used to practice the present invention.

The invention described herein could be used in conjunction with any type of visual field tester or other device containing a gaze tracker. One such system is illustrated in FIG. 1. A subject 101 is shown observing a hemispherical projection screen 102. The subject is instructed to fixate at a point at the center of the hemispherical screen 103. A projector 104 under control of a processor 105 projects a series of test stimuli 106 onto the screen. The subject indicates that a stimulus 106 was seen by depressing button 107. The response is recorded by processor 105. A camera 108 can be used to capture the gaze of the patient throughout the test. The images from the gaze camera can optionally be displayed on display 110 to the clinician for aid in patient alignment or test verification. A trial lens holder 109 is positioned in front of the eye of the subject being tested to correct the refractive error of the subject. One or more light sources 111 may be positioned in front of the eye of the subject, which create reflections from ocular surfaces such as the cornea. In one variation, the light sources may be light-emitting diodes (LEDs). While FIG. 1 shows a projection type visual field tester, the invention described herein can be used with other types of devices, including those that generate images through LCD or other displays. (See for example U.S. Pat. No. 8,132,916 to Johansson, hereby incorporated by reference.)

The camera can record and store one or more images of the eye during each stimulus presentation. This may lead to the collection of anywhere from tens to hundreds of images per visual field test, depending on the testing conditions. Alternatively, the camera may record and store a full length movie during the test and provide time stamps when each stimulus is presented. Additionally, images may also be collected between stimulus presentations to provide details on the subject's overall attention throughout the test's duration.

Eliminating the Initial Calibration Step

Figure 2A:
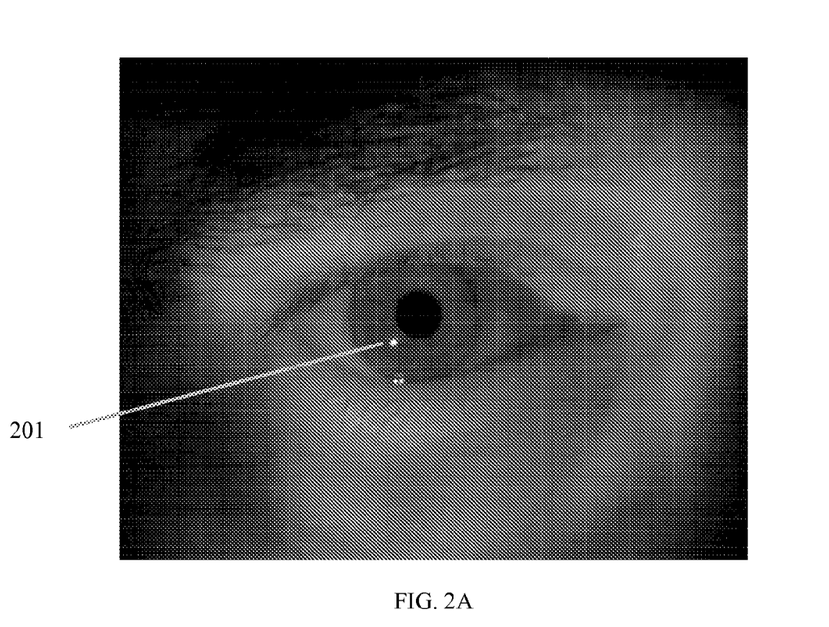
FIG. 2A shows an image of the eye having a reflection created by one LED.

The subject's gaze is characterized by the ocular surface reflection or reflections created by the one or more light sources, which are used in the definition of a gaze descriptor. In a preferred embodiment, the gaze descriptor is a vector extending from the center of the pupil to a reflection from the external surface of the cornea, created by a light source. FIG. 2A shows an eye having a reflection 201 created by one LED. To determine the gaze descriptor, first, the corneal reflex or reflexes and pupil are segmented from each image or images corresponding to each stimulus, as described below. In other embodiments, reflections from other ocular surfaces may be used, such as reflections from the back surface of the cornea, the front or back surfaces of the crystalline lens, or from the conjunctiva or sclera, for example.

Because ocular reflections appear as bright dots in the image, as seen in FIG. 2A, the initial candidate regions for ocular reflections can be identified using a thresholding scheme. Connected components analysis can then be performed on the thresholded image to refine the candidate set to regions that are within a predefined expected reflex size and to determine the centroid of the reflexes. In some variations of the method, the desired segmentation may then be selected based on further analysis of the geometries of the candidate regions. For example, we could look at the circularity of the candidate regions to select the most circular candidate. We could also look at the area of the candidate regions to eliminate stray reflections that do not correspond to valid size ranges expected from the LED reflexes. In variations of the method in which multiple illuminators are used, the known configuration of the illuminators can be used to tailor the region of interest for the segmentation of each reflex. In some embodiments using multiple illuminators, all of the illuminators may create simultaneous ocular reflections, and all of the reflections may be segmented from the same image. Alternatively, segmentation and identification of individual reflections may be simplified by individually turning on each illuminator in a particular order, synced with image capturing.

In the method described here, the pupil segmentation is performed using an image taken using illuminator configurations making the pupil appear dark compared to the iris. The illuminators used to create the ocular reflexes can be used for the illumination needed to capture an image of the eye. Once the image is acquired, first the approximate location of the pupil is determined using thresholding, since the pupil is dark compared to the iris. Connected components analysis can then be performed on the thresholded image. Information about the expected relative locations of the pupil and the segmented reflexes can also be used to aid in segmentation. Then, one row of the image at the initial estimate of the y-coordinate of the pupil center is analyzed to determine the left and right edges of the pupil using intensity gradients along this line. The left and right edges are then used to refine the x-coordinate of the pupil. One column of the image at this x-coordinate is then analyzed to determine the bottom edge of the pupil based on intensity gradients. This process can be repeated for a few rows near the center location. Based on the left, right, and bottom edges found, an estimate of the center of the pupil and radius can be calculated. In some variations, the top edge may also be found; but in the preferred variation the top edge is not used because subjects may have droopy eyelids that block the top edge of the pupil. The method described here assumes a circular model for the pupil, but in other embodiments, methods that fit an ellipse to the edges of the pupil could also be used, depending on availability of computational resources available for the task. In other embodiments, different pupil segmentation algorithms can be used. For example, active illumination methods can be used. These rely on "light" field-"dark" field images that capture a light pupil and a dark pupil using different illuminator configurations; the difference between the two images allows for pupil segmentation.

Figure 2B:
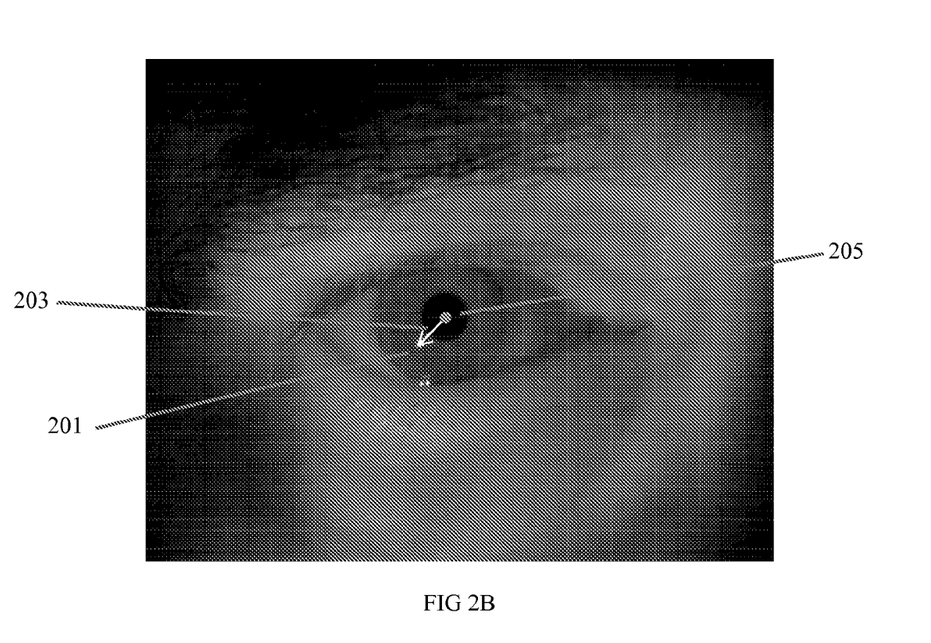
FIG. 2B shows an image of the eye having a reflection created by one LED, with the pupil center-reflex vector indicated.

Based on the pupil center found as described above and the segmentation of ocular reflex position, pupil center-reflex vectors are then determined for each stimulus, as shown in FIG. 2B. The pupil-center reflex vector 203 is defined as the vector extending from the pupil center 205 to the corneal reflex 201. The pupil-center reflex vector makes up the gaze descriptor, and is then stored for each stimulus. In one embodiment, the vectors may be stored based on their magnitude and angle from the x or y axis. In another embodiment, the pupil center-reflex vectors may be stored based on their components in the x and y directions.

Figure 3:
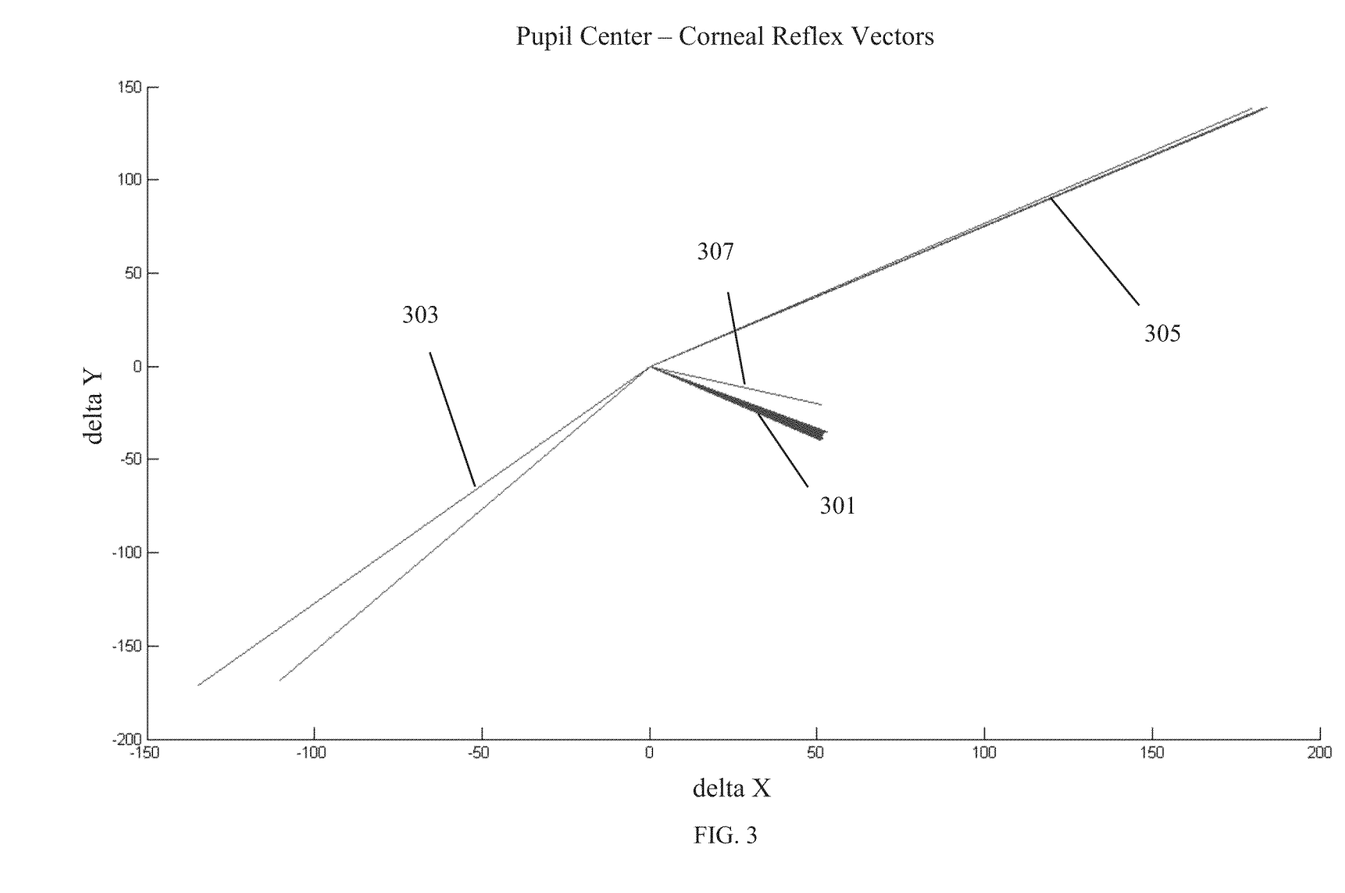
FIG. 3 shows pupil-reflex vectors from a set of 50 stimuli presentations.

A group of N gaze descriptors are used to identify the approximate pupil center-reflex vector corresponding to central fixation (referred to here as the "zero-calibration vector"). Because the subject has been instructed to fixate at a central location, it can be assumed that the majority or plurality of the N gaze descriptors will correspond to the subject's fixation at the central location. Based on this assumption, the group of N gaze descriptors can be analyzed to determine inlier and outlier vectors, where the inlier vectors approximate the zero-calibration vector, and the outlier vectors correspond to off-center fixation. FIG. 3 illustrates pupil center-reflex vectors for a series of 50 stimuli. Using an algorithm to identify the inlier and outlier vectors, the pupil center-reflex vectors falling in cluster 301 are identified as the inliers. The vectors falling into clusters 303, 305, and 307 are identified as the outliers. The vectors identified as outliers can be assumed to be associated with test stimuli during which the subject's gaze was off center.

A number of different algorithms can be used to identify the inliers and outliers. For the data shown in FIG. 3, cluster analysis was used to identify the inlier and outlier vectors. However, other algorithms may be used. For instance, inliers and outliers may also be identified by fitting a model to the data with robust estimators, such as the M-estimator, using weighted cost functions that weight the outliers and the inliers differently, or a robust model-fitting method such as RANSAC (Random Sample Consensus). The zero-calibration vector is then determined from the inlier vectors. In one variation, the zero-calibration vector may be a simple mean or median of the inlier vectors. In other variations, the zero-calibration vector may be an estimation of the vector based on the robust fitting methods referred to above.

The group of N gaze descriptors used to determine inliers and outliers may include the gaze descriptors for all of the test stimuli presented, or it may contain gaze descriptors for a subset of the test stimuli. For example, in one embodiment the group of N gaze descriptors may be a group made up of the first N vectors collected during the test. More specifically, the group could be made up of the first ten gaze descriptors out of a full test set of one hundred. In another variation the group of N gaze descriptors may include a larger number of gaze descriptors. In some variations the N gaze descriptors may be randomly selected from the entire set of test gaze descriptors, or the gaze descriptors may be selected from specific time points. In some instances, number N may be chosen on the basis of their agreement of the selected vectors. That is, the agreement between a certain number of gaze descriptors may be determined; if the vectors are found to be in close agreement, the zero-calibration vector is calculated from the acquired vectors. If the gaze descriptors are insufficiently similar, more gaze descriptors may be added to the analysis. This process may be repeated until the gaze descriptors are in close agreement. In some variations, there may an upper limit on the number of gaze descriptors that may be added to the analysis; in other variations, all gaze descriptors may be added if needed. Additionally or alternatively, the degree to which the inlier vectors align with each other may be used to estimate the precision of the calibration.

In other embodiments, determination of the zero-calibration vector may be based in full or in part on a previously acquired gaze descriptors for the same subject, such as ones obtained during one or more previous clinical examinations performed on the subject. In some variations, a previously acquired zero-calibration vector may be used as the zero-calibration vector in the current testing protocol. In other variations, a previously acquired zero-calibration vector may be used as an initial estimate of the zero-calibration vector at the beginning of the testing protocol, and may then be updated as more gaze descriptors are collected. In yet other variations, a previously acquired zero-calibration vector or a set of previously acquired gaze descriptors may be factored into the determination of inlier and outlier gaze descriptors during the current protocol. For instance, a previously acquired zero-calibration vector may be used as a Bayesian prior for estimating a new zero-calibration vector, or a previously acquired set of gaze descriptors may be added to the currently acquired set of gaze descriptors in the determination of inlier and outlier gaze descriptors. In some variations, in place of or in addition to previously acquired gaze descriptors for the same subject, a reference zero-calibration vector based on a single reference eye or on a compilation of reference eyes can be used. In some variations, the reference eyes can comprise the eyes of previous subjects.

The analysis of the group of N gaze descriptors to determine inliers and outliers may be carried out at different times during the testing protocol. For instance, it may be carried out as soon as the images for the group of N stimuli have been collected, or after data collection is complete. As another example, the zero-calibration vector may be estimated early in the examination or be initially based upon calibrations obtained during earlier examinations of the subject, and then updated as the examination proceeds, with a final estimate being calculated only after the examination has been completed. In this manner, technicians administering the examination may have the benefit of gaze direction information even from the very beginning of the examination, with more accurate final estimates later provided.

Once the zero-calibration vector is determined, the pupil center-reflex vector corresponding to test stimuli can then be compared to the zero-calibration vector to determine whether the subject was fixated on the central point during the stimuli. In one variation, the zero-calibration vector can be subtracted from a pupil center-reflex vector corresponding to a test stimulus, and the magnitude of the resulting vector can be used to quantify the relative deviation from central fixation. In some variations, when the magnitude of the resulting vector is above a certain threshold, the subject's gaze can be considered to be off center for the corresponding test stimulus presentation. The information regarding whether the subject's gaze was centrally fixated can be used in a number of ways. For instance, data for stimuli during which the gaze was not centered can be disregarded or flagged for the clinician, or the overall proportion of stimuli with off-center gazes can be reported. The zero-calibration vector can also be used in conjunction with other calibration data to estimate gaze direction, as described in more detail below.

Increasing the Accuracy of Gaze Estimation

As described above, gaze tracking in perimetry testing may be based on a set of calibration data from a single reference eye that is applied to all subjects undergoing testing. For each eye undergoing perimetry testing, a single-location zero-calibration is done to determine a pupil center-reflex vector associated with central fixation. This vector is then subtracted from subsequent pupil center-reflex vectors acquired during the presentation of test stimuli, and the result is inputted into a mapping function for the reference eye to estimate the gaze. However, this approach can be inaccurate because the mapping function depends on the shape of the eye and its anatomy, and thus the mapping function based on a single reference eye does not accurately estimate gaze for all eye shapes. Here, we improve accuracy without the need for individual subject calibration during the visual field testing protocol.

Figure 4:
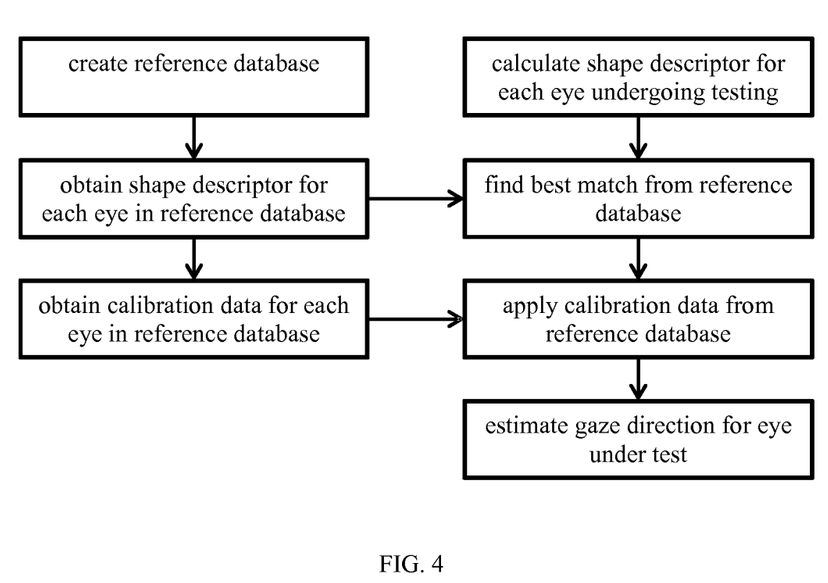
FIG. 4 illustrates the method for improving gaze tracking accuracy.

In one embodiment, the method described here uses a database of reference eyes instead of relying upon a single reference eye calibration. FIG. 4 illustrates this embodiment. Briefly, a reference database of eyes is first created. For each reference eye, a shape descriptor and calibration data are calculated. The reference database is stored for future use. When visual field testing is performed on a subject, the shape descriptor for the subject's eye is calculated and compared to the reference database to find the best match. The calibration data from the best match is then used to determine the subject's gaze. These steps are described in more detail below.

The reference database may have a number of different reference eyes, including eyes with different curvatures and/or pathologies. In one variation, the reference database may have about ten reference eyes containing, for instance, eyes with low curvature, medium curvature, and high curvature; various ranges of corneal eccentricities, since corneas tend to be ellipsoidal in shape, rather than perfectly spherical; disease states and healthy states; and so on. In other variations, the reference database may have more or fewer reference eyes. For each eye, the reference database contains a shape descriptor and a set of calibration data, which are described in more detail below.

Figure 5A:
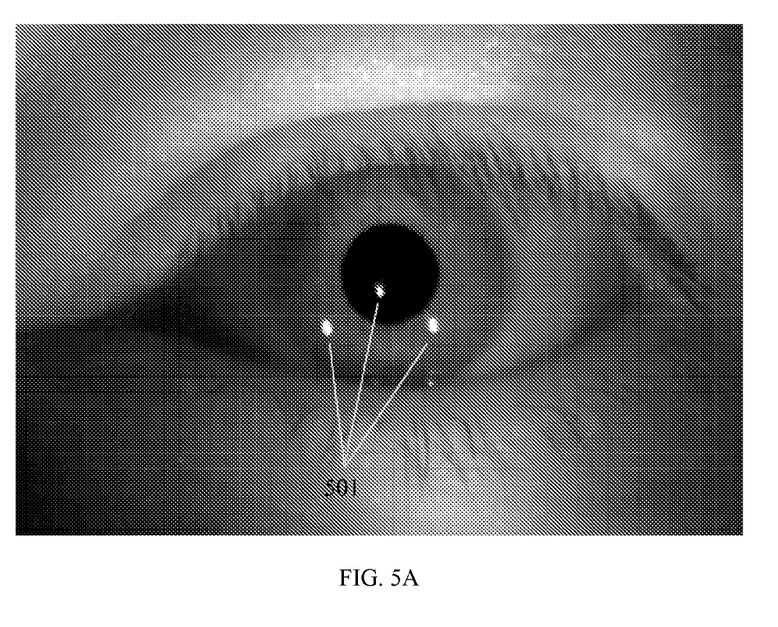
FIG. 5A shows an image of the eye have reflections created by three LEDs.

The shape descriptor, $S_i$, is given for each eye, where i is the index of the eye in the reference database. The shape descriptor can be defined by the relationship between the position of the pupil center and one or more ocular reflexes. To determine the shape descriptor for a reference eye, a reference subject can be told to fixate on a central point of a visual field testing system, such as the one shown in FIG. 1, containing one or more illuminators. The illuminators create reflections from an ocular surface. FIG. 5A shows the reflections in a preferred embodiment, where the visual field testing system contains three LEDs, with one LED located at the central fixation location, and two located below the central fixation location and pointed upwards toward the eye. This creates three reflections 501 from the cornea, which are recorded in an image of the eye, as shown in FIG. 5A. In other variations, any number or type of illuminators could be used, and/or they could be arranged in different configurations. In addition, in other embodiments, reflections from other ocular surfaces may be used, such as reflections from the back surface of the cornea, the front or back surfaces of the crystalline lens, or from the conjunctiva or sclera, for example.

Figure 5B:
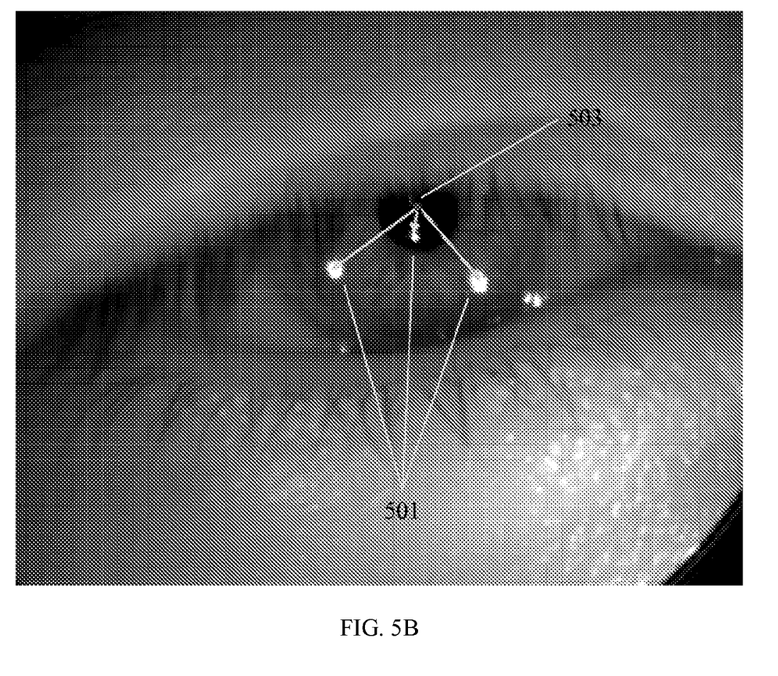
FIG. 5B shows an image of an eye having reflections created by three LEDs, with the pupil center-reflex vectors indicated.

The image of the pupil and ocular reflexes can then be used to determine the shape descriptor. The pupil and reflections are segmented out of the image and the center of the pupil is determined using the algorithms for segmentation and center determination described above. There are several different ways that the relationship between the positions of the pupil center and the ocular reflexes can be characterized to define the shape descriptor. In a preferred embodiment, as shown on a reference eye in FIG. 5B, the pupil center 503 is used as the origin, and individual vectors to each of the reflexes 501 are determined. These three vectors form the shape descriptor $S_i$, which is stored as described above. Using the pupil center as the origin has the advantage that the shape measurement is robust against translations of the head, but other shape descriptors can be used. Those skilled in the art can come up with other shape descriptors that could be used with this invention. For example, instead of a number of point illuminations, concentric circle illuminations could be used. This would allow capture of the corneal topography, and the relationship between the concentric rings reflected by the cornea could be used as a shape descriptor.

In addition to a shape descriptor, a set of calibration data is also acquired for each eye in the reference database. The calibration data consists of gaze descriptors that are correlated to specific gaze directions; the relationship between the gaze descriptors and the gaze directions is characterized by a mapping function. The calibration data may be acquired using the same perimetry system describe above, using one or more illuminators to create reflections from an ocular surface. In a preferred embodiment, one reflection is created on the cornea using one illuminator. Images of the eye are recorded while having the reference subject fixate at different locations—for instance, at each point in a three-by-three, four-by-four, or five-by-five grid. The pupil center and corneal reflex can then be segmented from each of the images corresponding to a particular stimulus location, as described above. A gaze descriptor for each different fixation point can then be defined based on the relationship between the pupil center and the ocular reflex. The relationship can be characterized in a number of ways, but in a preferred embodiment, the gaze descriptor can be based on the difference between the zero-calibration vector and the pupil center-reflex vector when the gaze is off center. The zero-calibration vector can be established as a first step in the test or can be estimated using the inlier/outlier technique described above.

Mapping functions between the gaze descriptors and gaze directions for each eye in the reference database can be generated. In one variation, this mapping function is a quadratic mapping function as shown below:

$$x_g = a_0 + a_1 v_x + a_2 v_y + a_3 v_x v_y + a_4 v_x^2 + a_5 v_y^2$$

$$y_g = b_0 b_1 v_x + b_2 v_y + b_3 v_x v_y + b_4 v_x^2 + b_5 v_y^2$$

where $(v_x, v_y)$ is the gaze descriptor and $(x_g, y_g)$ is the actual gaze direction. The above system is defined with 12 parameters, and requires measurements from a sufficient number of calibration points to determine the parameters. For example, since each calibration point defines 2 equations, a grid of 3×3 calibration points provides 18 equations, allowing the system to be solved using least squares method. Because the set of parameters a and b are independent, the system can also be solved as 2 sets of 6 variables using 9 equations.

The reference database can be built prior to a subject undergoing visual field testing, and thus can be created without adding to the procedure time for the subject. Moreover, the data can be acquired under controlled conditions, and can be acquired without hard constraints on the time taken to generate the database.

Once the reference database is built, it can then be used to determine a subject's gaze during visual field testing. When a subject undergoes visual field testing, the shape descriptor for the subject's eye is first determined using the same method used to determine the shape descriptors for the reference eyes, described above. The subject eye's shape descriptor is then compared to the shape descriptors for each of the reference eyes in the reference database to determine the best match. The best match can be determined by comparing the vectors in the reference shape descriptors to the vectors in the subject's shape descriptor. The comparison may be done via a number of different methods, including the Euclidian distance function, Manhattan distance function, cosine similarity measure, or similar vector comparison measures. In another variation, rather than finding a single best match, two or more reference eyes can be selected as the nearest matches. The calibration data (gaze descriptors and actual gaze locations) for each of the two or more reference eyes can then be used to create a new mapping function that can be used for the current eye under test. Because the best match can be determined very quickly, doing so does not add significantly to procedure time.

Once the best match is determined, its mapping function can be used to estimate the gaze of the subject's eye during the presentation of test stimuli. During the subject's perimetry testing, the same gaze descriptor as described above is determined during the presentation of each test stimulus, using the relationship between the pupil center and ocular reflexes. In one variation, this may require an initial step of determining the zero-calibration vector. Once the zero-calibration vector is determined, the difference between it and the pupil center-reflex vectors during stimuli presentation can be used to define the gaze descriptors for each of the test stimuli. In another embodiment, instead of independently determining the zero-calibration vector by having the subject fixate on a central point, the method described above for determining the zero-calibration vector without a separate initialization step can be used. The subject's gaze descriptor corresponding to each test stimulus is then inputted into the mapping function for the match in the reference database to estimate the gaze direction of the subject's gaze.

In another embodiment, the estimation of gaze direction may be based in full or in part on previously acquired calibration data for the same subject. Because calibration data for gaze direction is largely based on the anatomy of the subject's eye, calibration data acquired during a previous procedure will generally be usable for estimating gaze during a subsequent visit. In some variations, one or more sets of previously acquired calibration data, or a mapping function determined therefrom, can be used to as the calibration data to estimate the subject's gaze during the current testing session. In other variations, the previously acquired calibration data, or a mapping function determined therefrom, can be used to initially estimate gaze until an updated calibration is determined. In yet other variations, the previously determined calibration information may be used as a Bayesian prior for the current calibration. In some variations, the suitability of using previously acquired calibration data for the current testing session may be verified by comparing the shape descriptor for the subject's eye, determined as described above, between the two or more testing sessions.

The information regarding whether the subject's gaze was centrally fixated, and/or the direction of the subject's gaze during the presentation of each stimulus in the visual field test can be used in a number of ways. For instance, data for stimuli during which the gaze was not centered can be disregarded or flagged for the clinician, or the overall proportion of stimuli with off-center gazes can be reported in a report of the overall test results. The actual gaze location can be used to modify the test results including excluding test results that correspond to stimulus presentations during which the subject was not fixated on the central location. Additionally or alternatively, the gaze direction information can be used to adjust the test results to reflect the portion of the visual field where the stimulus was actually located, given the subject's gaze, or it can be used to adjust the placement of future test stimuli.

Although the invention is described here as applied to perimetry testing, it could be applied during any other application that requires gaze monitoring, particularly ones in which there are time constraints that make individual calibration for each eye undesirable. For example, the invention described here could be used in applications related to human-computer interaction.

The following References are Hereby Incorporated by Reference

Patent References

U.S. Pat. No. 3,718,386 to Lynn. "Automatic Visual Field Examination Including Fixation Monitoring and Compensation."
U.S. Pat. No. 3,883,235 to Lynn. "Automatic Visual Field Examination Including Fixation Monitoring and Compensation."
U.S. Pat. No. 7,809,160 to Vertegaal. "Method and apparatus for calibration-free eye tracking using multiple glints or surface reflections"
U.S. Pat. No. 7,306,337 to Ji. "Calibration-free gaze tracking under natural head movement"
U.S. Pat. No. 8,132,916 to Johansson. "High precision contrast ratio display for visual stimulus."
U.S. Pat. No. 6,367,932 to Donaldson. "Apparatus and method for visual field testing."
U.S. Pat. No. 5,491,757 to Lehmer et al. "Field tester gaze tracking using content addressable memories to improve image data analysis speed."
U.S. Pat. No. 5,220,361 to Lehmer et al. "Gaze tracking for field analyzer."
U.S. Publication No. 2012/0274905 to Johansson et al. "Systems and methods for improved visual field testing."
U.S. Publication No. 2010/0149488 to Lo et al. "Apparatus and method for objective perimetry visual field test."

Non-Patent References

Hu-chuan Lu, Chao Wang & Yen-Wei Chen, "Gaze Tracking by Binocular Vision and LBP Features." International Conference on Pattern Recognition (2008).

We claim:

1. A method for determining when the gaze of a subject is centered during visual field testing, wherein the subject has been instructed to fixate on a central location throughout the test, comprising:
    using one or more light sources to create one or more reflections from an ocular surface;
    displaying a series of test stimuli to the subject;
    collecting responses to the stimuli from the subject;
    imaging the subject's eye while each test stimulus is displayed;
    determining gaze descriptors for the eye for each test stimulus by analyzing the reflections of the light sources in the image, said gaze descriptors being defined by a vector extending from the reflection on the ocular surface to the center of the pupil of the eye;
    grouping all or a subset of the gaze descriptors into inlier or outlier gaze descriptors using an algorithm that assumes that the majority of the gaze descriptors correspond to the subject being fixated on the central location, with the inlier gaze descriptors corresponding to the subject's gaze being fixed on the central location and the outlier gaze descriptors corresponding to the subject's gaze being off-center from the central location;
    determining a zero calibration vector based on the inlier gaze descriptors;
    comparing the gaze descriptor determined for each test stimulus to the zero-calibration vector to determine the deviation of the gaze from the central location; and
    for any response to the stimuli where the associated deviation from the zero calibration vector exceeds a threshold performing one of the following steps:
        (a) disregarding the response;
        (b) flagging the response to a clinician; or
        (c) reassigning the response to a different location.

2. A method for determining a subject's gaze direction during a visual field test, comprising:
    storing in a database shape descriptors and associated calibration data for a plurality of reference eyes having different curvatures, said calibration data including a mapping function that maps gaze descriptors to gaze directions for the reference eyes;
    using one or more light sources to create one or more reflections from an ocular surface;
    determining a shape descriptor for the subject's eye based on the locations of the reflections from the ocular surface;
    comparing the shape descriptor for the subject's eye to predetermined shape descriptors associated with the reference eyes in the database to determine one or more matches;
    displaying a series of test stimuli to the subject;
    collecting responses to the stimuli from the subject;
    imaging the subject's eye while each test stimulus is displayed;
    determining a gaze descriptor for the subject's eye for each test stimulus by analyzing the reflections of the light sources in the image; and
    inputting the gaze descriptor for the subject's eye for each test stimulus into said mapping function determined from the one or more matched reference eyes to determine the subject's gaze direction during each test stimulus.

3. A method as recited in claim 1, wherein the step of determining gaze descriptors is only performed in conjunction with the display of test stimuli to the subject.

4. A method as recited in claim 1, wherein the gaze descriptor comprises one or more vectors from the pupil center to the one or more reflections from an ocular surface.

5. A method as recited in claim 1, wherein the inlier and outlier gaze descriptors are determined by cluster analysis, or by robust model fitting methods.

6. A method as recited in claim 1, further including the step of disregarding responses to the stimuli where the associated deviation from the zero calibration vector exceeds the threshold.

7. A method as recited in claim 1, wherein the inlier and outlier gaze descriptors are determined using all of the gaze descriptors.

8. A method as recited in claim 1, wherein the inlier and outlier gaze descriptors are determined using a subset of the gaze descriptors.

9. A method as recited in claim 1, wherein the zero calibration vector is determined partially or completely on the basis of vector congruity, or on the basis of prior calibrations of the same eye, or on the basis of zero-calibration vectors for one or more reference eyes.

10. A method as recited in claim 1, wherein the zero calibration vector is compared to the gaze descriptors of test stimuli to determine a relative magnitude of gaze deviation from the central location.

11. A method as recited in claim 1, wherein the zero calibration vector is compared to the gaze descriptors of test stimuli to determine a direction of gaze deviation from the central location.

12. A method as recited in claim 1, further comprising:
    using a previously determined zero-calibration vector for the subject as an initial estimate of a zero-calibration vector for the current test; and
    refining the initial estimate of a zero-calibration vector for the current best based on the determination of inlier gaze descriptors.

13. A method as recited in claim 1, wherein determining the inlier and outlier gaze descriptors uses information from one or more previous calibrations of the same eye, or information from one or more reference eyes.

14. A method as recited in claim 2, wherein three light sources are used to create reflections from the subject's cornea.

15. A method as recited in claim 2, wherein the shape descriptors for the subject's eye and for the plurality of reference eyes are determined based on a relationship between the locations of the pupil center and the one or more reflections from an ocular surface when the subject or reference subject is fixated on a particular location.

16. A method as recited in claim 2, wherein the set of reference eyes comprises eyes having different corneal topologies.

17. A method as recited in claim 2, wherein the one or more matches are determined by the Euclidian distance function, Manhattan distance function, cosine similarity measure, or another vector similarity measure.

18. A method as recited in claim 2, wherein the shape descriptor for the subject's eye is compared to predetermined shape descriptors for a set of reference eyes to determine more than one match.

19. A method as recited in claim 2, wherein the gaze descriptor for the subject's eye for each test stimulus is determined based on the relationship between the location of the pupil center and one or more reflections from an ocular surface.

20. A method as recited in claim 2, further comprising determining the mapping function for each of the reference eyes.

21. A method as recited in claim 15, wherein the subject or a reference subject is fixated on a central location.

22. A method as recited in claim 15, wherein each shape descriptor comprises one or more vectors from the pupil center to the one or more reflections from the cornea.

23. A method as recited in claim 18, further comprising combining the calibration data for each of the matches to create a composite mapping function.

24. A method as recited in claim 19, wherein the gaze descriptor comprises one or more vectors from the pupil center to the one or more reflections from the subject's cornea.

25. A method as recited in claim 20, wherein determining the mapping function for each of the reference eyes comprises determining a gaze descriptor for each reference eye at each of a series of fixation locations.

26. A method as recited in claim 25, wherein the series of fixation locations comprises points on a three-by-three grid.

27. A method as recited in claim 25, wherein the series of fixation locations comprises points on a five-by-five grid.

\* \* \* \* \*